(12) United States Patent
Sigal et al.

(10) Patent No.: US 9,448,235 B2
(45) Date of Patent: Sep. 20, 2016

(54) METHODS AND APPARATUS FOR IMPROVED LUMINESCENCE ASSAYS USING MICROPARTICLES

(75) Inventors: George B. Sigal, Rockville, MD (US); Jacob N. Wohlstadter, Rockville, MD (US); Satyanarayana Gudibande, Gaithersburg, MD (US); Mark T. Martin, Rockville, MD (US); James L. Wilbur, Germantown, MD (US)

(73) Assignee: MESO SCALE TECHNOLOGIES LLC., Rockville, MD (US)

( * ) Notice: Subject to any disclaimer, the term of this patent is extended or adjusted under 35 U.S.C. 154(b) by 0 days.

(21) Appl. No.: 12/591,528

(22) Filed: Nov. 23, 2009

(65) Prior Publication Data

US 2010/0140086 A1 Jun. 10, 2010

Related U.S. Application Data

(60) Division of application No. 10/884,536, filed on Jul. 2, 2004, now Pat. No. 7,682,788, which is a continuation of application No. 09/896,962, filed on Jun. 29, 2001, now Pat. No. 6,846,629, which is a continuation of application No. 08/998,137, filed on Dec. 23, 1997, now Pat. No. 6,319,670.

(51) Int. Cl.
| | |
|---|---|
| G01N 27/26 | (2006.01) |
| G01N 33/543 | (2006.01) |
| B82Y 30/00 | (2011.01) |
| C07H 21/00 | (2006.01) |
| C12Q 1/68 | (2006.01) |
| G01N 33/532 | (2006.01) |
| G01N 33/533 | (2006.01) |
| G01N 33/58 | (2006.01) |

(52) U.S. Cl.
CPC ......... *G01N 33/54346* (2013.01); *B82Y 30/00* (2013.01); *C07H 21/00* (2013.01); *C12Q 1/6816* (2013.01); *C12Q 1/6825* (2013.01); *C12Q 1/6834* (2013.01); *G01N 33/532* (2013.01); *G01N 33/533* (2013.01); *G01N 33/5438* (2013.01); *G01N 33/54306* (2013.01); *G01N 33/54366* (2013.01); *G01N 33/582* (2013.01); *G01N 33/587* (2013.01); *C07B 2200/11* (2013.01); *G01N 2458/30* (2013.01)

(58) Field of Classification Search
CPC ............................ C12Q 1/6806; C12Q 1/6813
USPC .............................................. 435/6, 6.1, 91.2
See application file for complete search history.

(56) References Cited

U.S. PATENT DOCUMENTS

| | | | |
|---|---|---|---|
| 4,372,745 A | 2/1983 | Mandle et al. | |
| 4,925,785 A | 5/1990 | Wang et al. | |
| 5,019,521 A | 5/1991 | Krupey | |
| 5,108,893 A | 4/1992 | Baret | |
| 5,124,246 A | 6/1992 | Urdea et al. | |
| 5,175,270 A | 12/1992 | Nilsen et al. | |
| 5,180,828 A | 1/1993 | Ghazarossian et al. | |
| 5,235,808 A | 8/1993 | Taylor | |
| 5,252,459 A | 10/1993 | Tarcha et al. | |
| 5,310,687 A | 5/1994 | Bard et al. | |
| 5,433,896 A | 7/1995 | Kang et al. | |
| 5,453,356 A | 9/1995 | Bard et al. | |
| 5,597,910 A | 1/1997 | Gudibande et al. | |
| 5,679,519 A | 10/1997 | Oprandy | |
| 5,744,367 A | 4/1998 | Talley et al. | |
| 6,096,500 A | 8/2000 | Oprandy et al. | |
| 6,207,369 B1 | 3/2001 | Wohlstadter et al. | |
| 6,319,670 B1 | 11/2001 | Sigal et al. | |
| 6,846,629 B2 | 1/2005 | Sigal et al. | |
| 7,682,788 B2 | 3/2010 | Sigal et al. | |

FOREIGN PATENT DOCUMENTS

| | | |
|---|---|---|
| EP | 0522677 | 1/1993 |
| EP | 0757252 | 2/1997 |
| WO | 87/06706 | 11/1987 |
| WO | 90/05301 | 5/1990 |
| WO | 92/14138 | 8/1992 |
| WO | 95/02700 | 1/1995 |
| WO | 96/21154 | 7/1996 |
| WO | 96/28538 | 9/1996 |
| WO | 96/35812 | 11/1996 |
| WO | 96/41175 | 12/1996 |

OTHER PUBLICATIONS

Blackburn et al. "Electrochemiluminescence detection for development of immunoassays and DNA probe assays for clinical diagnostics" Clin. Chem. 37:1534-1539 (1991).
Leland et al. "Electrogenerated chemiluminescence: An oxidative-reduction type ECL reaction sequence using tripropyl amine" J. Electrochem. Soc. 137:3127-3129 (1990).
Yang et al. "Electrochemiluminescence: A new diagnostic and research tool" Biotechnol. 12:193-194 (1994).

Primary Examiner — Cynthia B Wilder
(74) Attorney, Agent, or Firm — Nixon & Vanderhye PC

(57) ABSTRACT

A method and apparatus for performing electrochemiluminescence assays are presented. In exemplary embodiments of the present invention an apparatus comprises an ECL-inactive electrode surface having a first assay-ligand immobilized thereon and an ECL-active microparticle having a second assay ligand immobilized thereon. In exemplary embodiments of the present invention a method comprises (a) forming a mixture comprising an electrochemiluminescent label and a microparticle having a first assay-ligand immobilized thereon, (b) applying electrochemical energy to an electrode surface in the presence of said mixture, and (c) measuring emitted electrochemiluminescence, where the microparticle is ECL-active and where the electrode surface is ECL-inactive when electrochemical energy is applied to it in the presence of said mixture.

18 Claims, 4 Drawing Sheets

METHODS AND APPARATUS FOR IMPROVED LUMINESCENCE ASSAYS USING MICROPARTICLES

CROSS-REFERENCE TO RELATED APPLICATION

This application is a divisional of Ser. No. 10/884,536, filed Jul. 2, 2004, now U.S. Pat. No. 7,682,788; which is a continuation of Ser. No. 09/896,962, filed Jun. 29, 2001, now U.S. Pat. No. 6,846,629, which is a continuation of Ser. No. 08/998,137, filed Dec. 23, 1997, now U.S. Pat. No. 6,319,670; each of which is hereby incorporated herein by reference.

FIELD OF THE INVENTION

This application relates generally to methods and compositions for conducting binding-assays, more particularly to those which measure the presence of an analyte of interest by measuring electrochemiluminescence emitted by one or more labeled components of the assay system. More specifically, the invention relates to precise, reproducible, accurate homogeneous or heterogeneous specific binding assays of improved sensitivity using electrochemiluminescent components.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescence is triggered by a voltage imposed on a working electrode at a particular time and in a particular manner. The light produced by the label is measured and indicates the presence or quantity of the analyte. For a fuller description of such ECL techniques, reference is made to U.S. Pat. No. 5,221,605, U.S. Pat. No. 5,591,581, U.S. Pat. No. 5,597,910, PCT published application WO90/05296, PCT published application WO92/14139, PCT published application WO90/05301; PCT published application WO96/24690, PCT published application US95/03190, PCT application US97/16942, PCT published application US96/06763, PCT published application WO95/08644, PCT published application WO96/06946, PCT published application WO87/06706, PCT published application WO96/33411, PCT published application WO96/39534, PCT published application WO96/41175, PCT published application WO96/40978, PCT/US97/03653 and U.S. patent application Ser. No. 08/437,348 (U.S. Pat. No. 5,679,519). The disclosures of the aforesaid applications are incorporated by reference. Reference is also made to a 1994 review of the analytical applications of ECL by Knight, et al. (Analyst, 1994, 119: 879-890) and the references cited therein. The disclosure of the aforesaid articles are also incorporated by reference.

While electrochemiluminescence assays are significantly improved over chemiluminescence, fluorescence, ELISA and radioisotope-based assays, as well as other assay techniques, there is always a desire to improve assays by increasing the signal or modulation signal obtained from a binding event. By doing so one can improve the ratio of signal to background noise and, therefore, the sensitivity of the assay. Increasing the signal of an ECL assay also has several instrumental advantages including the following: i) less sensitive (and less expensive) light detection systems are required; ii) smaller samples are required; iii) electrodes and instrumentation may be miniaturized so as to allow for instruments that are smaller and/or devices that run many assays concurrently in a small area.

OBJECTS OF THE INVENTION

1. It is therefore a primary object of this invention to provide methods, reagents and compositions, for conducting of electrochemiluminescence binding assays which improve one or more characteristics of the assay or the instruments used to conduct the assay.

2. It is a further and related object of this invention to increase the number of photons emitted per binding event in an electrochemiluminescence assay.

3. It is a further and related object of the invention to improve the sensitivity of electrochemiluminescence assay by increasing the signal and thereby increasing the ratio of signal to background.

4. It is still a further and related object of the invention to reduce the sensitivity requirements for the light detection system used in electrochemiluminescence instruments.

5. It is still a further and related object of the invention to miniaturize ECL electrodes and instrumentation and thereby decrease the size the instruments themselves.

6. It is still a further and related object of the invention to miniaturize ECL electrodes and instrumentation and thereby increase the number of assays that can be run concurrently in one device.

SUMMARY OF THE INVENTION

These and other objects of the invention are achieved using microparticles comprised of an electrically conductive material having (a) one or more copies of an assay ligand immobilized on its outer surface, and (b) a plurality of electrochemiluminescent moieties immobilized on its outer surface. The assay ligand may be linked to the electrochemiluminescent moiety. More specifically, it has now been found that colloidal gold is a highly advantageous conductive material with which to form microparticles. Colloidal gold particles having one or more assay ligands immobilized on its outer surface and a plurality of ECL moieties immobilized on its outer surface can be used in a wide range of assay formats, including those based on detecting the ECL from moieties immobilized on the particle and those based on the modulation by the particles of the ECL from free ECL moieties in solution. The objects of the present invention may also be achieved using microparticles that do not comprise electrically conductive material.

Assays for an analyte of interest present in a sample are conducted by (a) forming a composition comprising (i) the sample, and one or more microparticles of the invention; (b) incubating said composition to form a complex; (c) causing the complex to bind to an assay-ligand immobilized on an electrode; and (d) conducting an electrochemiluminescence measurement in the presence of electrochemiluminescence reactants.

Assays employing bound ECL moieties can be carried out in a similar sequence of steps. The complex formed includes an assay ligand, the microparticle of the invention (wherein said microparticle contains ECL moieties) and the assay-ligand immobilized on the electrode so as to furnish a plurality of ECL moieties at the electrode. The electrochemiluminescence measurement is conducted there in the presence of reactants.

DETAILED DESCRIPTION OF THE INVENTION

Definition of Terms

"Assay-ligand" means a binding substance which may be an analyte or an analog thereof; a binding partner of the analyte or an analog thereof; additional binding partners of the binding partner or analog thereof; or a reactive component capable of reacting with the analyte, an analog thereof or a binding partner or analog thereof. These species can be linked to a combination of one or more binding partners and/or one or more reactive components and/or an analyte or its analog or a combination thereof. It is also within the scope of the invention for a plurality of the aforementioned species to be bound directly, or through other molecules to an analyte or its analog.

The term assay-ligand, therefore, includes analytes that can be measured by a binding assay, e.g., proteins (including oligopeptides, polypeptides, glycoproteins, lipoproteins and peptide analogs), nucleic acids (including mononucleotides, olignucleotides, polynucleotides, ribonucleic acids, deoxyribonucleic acids, and nucleic acid analogs), lipids, steroids, carbohydrates (including sugars and polysaccharides), porphyrins, alkaloids, nucleotides, nucleosides, amino acids, fatty acids, viruses, microorganisms, and biological cells (including prokaryotic and eukaryotic cells) and subcellular particles derived therefrom. The analytes may be, for example, antibodies, enzymes, receptors, ligands, hormones, pharmacological agents, cellular metabolites, toxins, pathogens, carcinogens, vitamins, transport proteins, structural proteins, cofactors, nucleic acid binding molecules, and nucleic acid sequences (including sequences characteristic of pathogens, disease states, or susceptibility to diseases). The "binding partner" or "additional binding partners of the binding partner" may be, for example, antibodies (e.g., antibodies that bind to the analyte, to other antibodies, to nucleic acids, or to haptens linked to an analyte or binding partner), haptens recognized by an antibody, ligands recognized by receptors, receptors, nucleic acids, nucleic acid binding compounds, avidin, streptavidin, or biotin (or a biotin-labeled macromolecule).

The term "ECL moiety" and "TAG" are used interchangeably to refer to labels or other reactants that can be induced to luminesce (or can be chemically transformed into species that luminesce) when electrochemically oxidized or reduced in an appropriate chemical environment. It is within the scope of the invention for the species termed "ECL moiety", and "TAG" to be linked to an assay ligand. The term "TAG1" is used to refer to ECL moieties comprising ruthenium tris(bipyridyl) and derivatives thereof. It is within the scope of the invention for a species termed "TAG1" to be linked to an assay ligand. The terms "ECL coreactant" or "coreactant" are used to refer to reagents or analytes that promote electrochemiluminescence from an ECL moiety.

The terms detection and quantitation are referred to as "measurement", it being understood that quantitation may require preparation of reference compositions and calibrations.

THE MICROPARTICLES OF THE INVENTION

Figure 1:
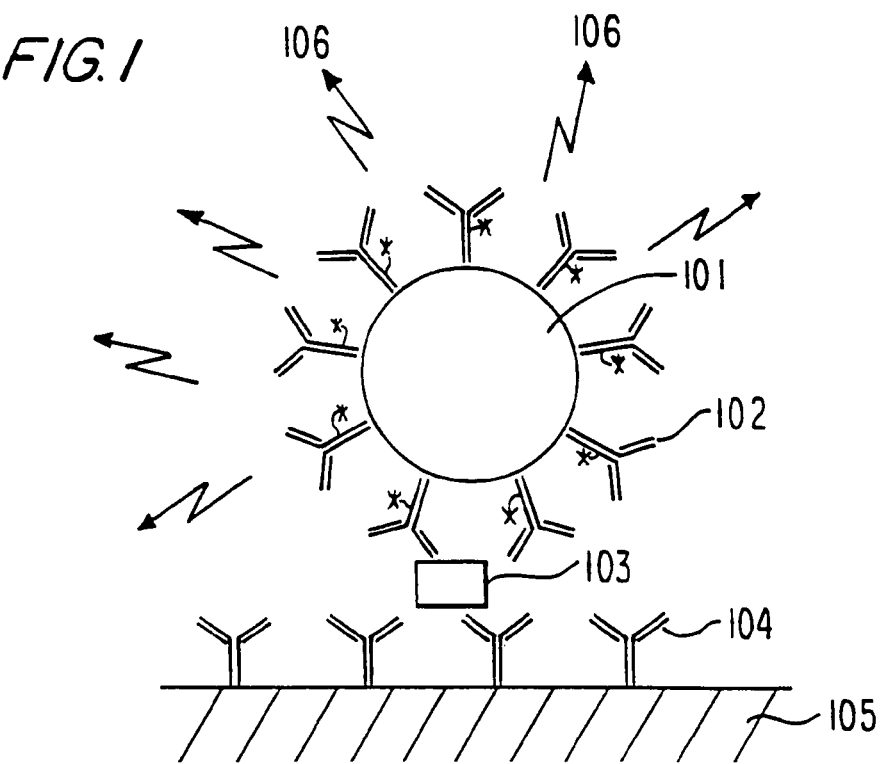
FIG. 1 is a schematic representation of a microparticle of the invention having antibodies immobilized upon it, wherein said antibodies are linked to ECL moieties, and a sandwich immunoassay employing that microparticle.

It has been found that significant benefits are achieved in electrochemiluminescence reactions using microparticles comprised of an electrically conductive material having (a) one or more copies of an assay-ligand immobilized on its outer surface and (b) a plurality of electrochemiluminescent moieties immobilized on its outer surface. The micro-particles may have a coating thereupon upon which the assay-ligand and electrochemiluminescent moieties are immobilized. In another embodiment the conductive microparticles have a plurality of copies of an assay-ligand labeled with an electrochemiluminescent moiety immobilized on its outer surface.

The microparticles of the invention are preferably comprised of a highly conductive and/or semiconductive material. In an especially preferred embodiment of the invention, the microparticles are colloidal gold particles. The preparation of conductive particles is well known in the art (see, e.g., *Nanomaterials: Synthesis, Properties, and Applications*, Edelstein, A. S. et al. Ed., Inst. Of Physics Publications: Philadelphia, 1996 and Fendler et al., *Adv. Mater.*, 1995, 7:607). For example, conductive microparticles may be prepared that comprise metals, for example, gold, silver, platinum, palladium, zinc, iron, nickel, lead, and copper (see, e.g., Bradley, J. S., *Clusters Colloids*, 1994, 459-544 and Frens, G., *Nature Physical Science*, 1973, 241:20-22).

The particles may comprise alloys of more than one metallic element. Conductive microparticles may comprise graphitic carbon (e.g., carbon black, graphitic nanotubes, or fullerenes); see, e.g., *Handbook of Carbon, Graphite, and Fullerenes*, Pierson, H. O., Ed., Noyes Publications, 1993; *Carbon Nanotubes*, Endo, M., Ed., Pergamon Pr.: Oxford, 1996; and U.S. Pat. No. 4,663,230. Conductive microparticles may comprise organic conductors, for example, polypyrrole, polythiophene, polyaniline, and polyacetylene (for a review of organic conductors see, e.g., *Conjugated Conducting Polymers*, H. Keiss, Ed., Springer-Verlag: New York, 1992; for a review of bioanalytical applications of some organic conductors, see, e.g., Barisci et al., *Trends in Polym. Sci.*, 1996, 4:307-311; for a description of colloids prepared from organic conductors, see, e.g., U.S. Pat. No. 5,252,459 and *Colloidal Polymer Particles*, Buscall, R., Ed., Academic Press: San Diego, 1995). The microparticles of the invention may comprise a semi-conductor, for example, a semi-conducting metal oxide. Some examples of semiconducting metal oxides that have been incorporated into microparticles include tin oxide (undoped or doped with antimony or indium), titanium oxide, zinc oxide, and cuprous oxide. Other semiconducting materials that have been incorporated into microparticles (see, e.g., Murray et al., *J. Am. Chem. Soc.*, 1993, 115:8706-8715) include silicon, cadmium sulfide, cadmium selenide, molybdenum sulfide, and zinc selenide. The microparticles may be entirely composed of one or more conducting and/or semiconducting materials or may also comprise an insulating material. For example, conducting and/or semiconducting particles have been formed by coating particles of an insulating material (e.g., silica) with, e.g., organic conductors, metals, or metal oxides (see, e.g., U.S. Pat. Nos. H001447, 5,512,094, 5,552,086, and 5,236,737).

The microparticles of the invention may have a wide variety of sizes and shapes. By way of example and not limitation, microparticles may be between 5 nanometers and 10 micrometers. Preferably microparticles have sizes between 20 nm and 200 nm. The particles may be spherical, oblong, rod-like, etc., or they may be irregular in shape.

The microparticles of the invention preferably comprise materials that are electrically conductive. In the context of this application, conductive materials are materials that have bulk resistivities of less than $1\times10^{13}$ Ωcm. We use the term "very highly conductive" to refer to particles comprising materials with bulk resistivities less than $1\times10^{-4}$ Ωcm. We use the term "highly conductive" to refer to particles comprising materials with bulk resistivities less than $1\times10^{-2}$ Ωcm. The invention also includes the use of microparticles comprising primarily non-conducting materials (e.g., silica, alumina, polystyrene, polyacrylates, polyacrylamides, ceramics, glasses and such). Microparticles of the invention may be solid or porous. Microparticles of the invention may also include macromolecules or aggregates thereof (e.g., a polymer, a dendrite, a polysaccharide, a protein, nucleic acids, or other biological macromolecules of appropriate size). Microparticles may be inanimate or alternatively, may include animate biological entities such as cells, viruses, bacterium and the like.

In one embodiment of the invention, the use of microparticles as labels provides for improved signal in ECL assays by providing a scaffold for multiple ECL moieties. While the use of binding reagents comprising multiple ECL moieties is known, the signal enhancement obtainable by that approach is limited for the following reasons: i) the number of labels that can be attached to a binding reagent is limited by the surface area of the reagent; ii) multiple labeling of a binding reagent may lead to denaturation and/or inactivation of the reagent; iii) multiple labeling of a reagent may interfere with its ability to bind other reagents, e.g., by blocking the active site; and iv) multiple labeling of a binding reagent may lead to quenching of the luminescent excited state of one or more labels due to crowding of the labels on one, e.g., protein or nucleic acid. By providing a scaffold for ECL moieties, said scaffold not being involved in the binding event and said scaffold having a large surface area compared to the binding reagent, microparticles reduce or eliminate the limitations stated above.

In certain embodiments of the invention, the use of microparticles as a scaffold for multiple ECL moieties provides for reduced non-specific binding between the ECL labels and/or i) other entities present in either the sample (e.g., proteins nucleic acid and the like); ii) the assay reagents (e.g., assay ligands); iii) the instrumentation/materials used to perform ECL assays (e.g., a solid support, an electrode, a cell, and the like). Reduced non-specific binding can advantageously improve the performance of assay measurements in several ways, for example: i) by decreasing background (non-specific) signals to improve sensitivity and/or dynamic range; ii) by reducing or eliminating the necessity for wash steps during the assay process (thus reducing the cost, time, and complexity of ECL assays and instrumentation); iii); by allowing a multiple of different assay ligands to be present in the same assay (or reaction) media without excessively interfering with each other or with other assay reagents or ECL instrument, and iv) by allowing more ECL moieties to be incorporated in an ECL label (without incurring undue nonspecific binding), thus increasing the number of photons emitted per binding event (which may improve sensitivity, dynamic range, and/or reduce the cost of complexity of light detectors used for ECL assays).

We have observed in many ECL assays using microparticles that the nonspecific binding has been unexpectedly low, even relative to the nonspecific binding observed for assay ligands labeled with ECL moieties, wherein the ligands are free in solution.

In certain embodiments, non-specific binding can be further reduced by appropriate modification of the microparticles. In one embodiment, the microparticle is coated with a substance (e.g., an oligo- or poly-ethylene glycol moiety) that resists adsorption of proteins (e.g., the coating of gold particles with oligo-ethyleneglycol terminated alkane thiolates is described by Weissbecker, et al., *Langmuir*, 1996, 12:3763-3772). Alternatively, the microparticle can be coated with a substance bearing hydrophilic or charged moieties. The coating of colloidal particles with such substances is a well-known method of preventing particles aggregation and is termed "steric stabilization", see, e.g., Sato et al., *Stabilization of Colloidal Dispersions by Polymer Adsorption*, Marcel Dekker, New York, 1980. In another embodiment, the microparticle may be coated with ECL moieties designed to reduce or resist non-specific binding of biological molecules (e.g., proteins, nucleic acid, or the like): such ECL moieties may incorporate for example, oligoethylene glycol moieties, hydrophilic moieties, and/or charged moieties. See, for example, published PCT US97/04150 for a description of some ECL moieties designed to reduce non-specific binding.

In a preferred embodiment of the invention, the microparticles are comprised of a conductive material, preferably a highly conductive material. The use of some conductive particles as scaffolds for ECL moieties can lead to additional enhancements in ECL when compared to certain non-conductive particles. Without being bound by theory, it is believed that this additional enhancement is due to the ability of the particle itself to conduct electrons from the working electrode so as to oxidize or reduce ECL moieties on its surface. In an especially preferred embodiment of the invention, the particles are comprised of a very highly conductive material.

In a preferred embodiment of the invention, the microparticles comprise a material capable of acting as a working electrode for inducing ECL from a certain ECL moiety and a particular ECL coreactant (i.e., the material is "ECL active"). It is possible to determine if a material is ECL active for a particular combination of ECL moiety and coreactant by testing whether a sample of the material, when used as a working electrode in an appropriate electrochemical cell under appropriate conditions, induces ECL. Using this testing procedure for selecting ECL-active and ECL-inactive materials for the generation of ECL from ruthenium-tris-bipyridyl in the presence of tripropylamine (TPA) we have found that gold, palladium, platinum, indium and antimony doped tin oxide, polythiophene, carbon electrodes and other materials are ECL-active. Certain other materials, under certain conditions, are ECL-inactive or only weakly ECL-active relative to other ECL active materials. Materials may be active with respect to one or more ECL labels and/or ECL coreactants and inactive with respect to one or more different ECL labels and/or coreactants.

The microparticle of the invention is preferably transparent to the wavelength of light emitted by the ECL label so that the microparticle does not block emitted light from reaching the light detector. Microparticles with this advantageous property may be selected by matching the absorption properties of the particles to the emission properties of the label. Conductive microparticles that transmit in the visible are known, e.g., tin oxide (preferably doped with indium or antimony) transmits light of most visible wavelengths. Another example, colloidal gold, absorbs green strongly but transmits orange and red.

The microparticle of the invention is preferably attached to an assay-ligand (e.g., a protein such as an antibody or receptor, a nucleic acid probe, or a small molecule analyte of interest such as a pharmacological agent or hormone). The attachment of molecules (e.g., proteins, nucleic acids, and small molecules) to microparticles is known in the art (see, for example, the following texts, all of which are included by reference: *Collidal Gold: Principles, Methods and Applications*, Vol. 1-3; Hayat, M. A. Ed., Academic Press: New York, 1989; *Immobilization of Enzymes and Cells*, Bickerstaff, G. F., Ed., Humana Press: Totowa, N.J., 1997; U.S. Pat. No. 5,252,459; and Mirkin et al. *Nature,* 1996, 382:607-609). The assay-ligand may be immobilized by adsorption on the particle. The adsorption of proteins and/or nucleic acids on microparticles, e.g., gold, silver, silica, polystyrene and such, is known. Nucleic acids and proteins can be adsorbed directly on metals, such as gold and platinum, that have surfaces that behave as soft acids (see, e.g., Flanagan et al., *Electron. Lett.,* 1984, 20:968-970). Proteins adsorb strongly to the surface of hard acids, e.g., oxides such as silicon dioxide, tin oxide, titanium oxide (see, e.g., Asanov et al., *J. Colloid Interface Sci.,* 1997, 191:222-235). Proteins and nucleic acids may also be adsorbed onto particles having hydrophobic or charged surfaces (e.g., unmodified polystyrene particles or polystyrene particles modified with charged moieties). Assay-ligands can be adsorbed onto surfaces by modification of the assay-ligands with moieties that are known to strongly adsorb on the surface, for example: thiols will facilitate adsorption on gold, hydrophobic groups will facilitate adsorption on hydrophobic surface (such as polystyrene), and charged groups will facilitate adsorption on surfaces of opposite charge). Assay-ligands may also be attached covalently onto the microparticles, for example, by the coupling of an assay-ligand comprising an activated silane to a silicon oxide or metal oxide surface or by the coupling of an assay-ligand to functional groups present on a polymeric particle.

Alternatively, the assay-ligand may be immobilized by adsorption and/or covalent attachment to a "binding layer" coated on the surface of the particle. For example, an assay-ligand may be covalently attached to an oxide surface (e.g., silica or tin oxide) by attachment to functional groups introduced on the surface of the particle (these functional groups may be introduced by methods well-known in the art, e.g., by coating the particle with a self-assembled layer of a functionalized monomer such as a silane. Similarly, an assay-ligand may be covalently attached to the gold surface of a gold particle by coating the particle by reaction with a functionalized thiol (e.g., to form a self-assembled monolayer), see, e.g., U.S. Pat. No. 5,384,073. Assay-ligands can be attached to microparticles by attachment to an adsorbed layer of material (e.g., a protein or a polymer), see, e.g., Mrsny et al., *Eur. J. Cell. Biol.,* 1988, 45:200. Preferably, coatings for conductive particles may have one or more of the following properties so as to promote the microparticle to act as an electrode for generating ECL: i) the binding layer is itself at least partially conductive; ii) the binding layer is thin (preferably <5 nm) and/or iii) the binding layer does not completely coat the surface of the microparticle (e.g., there are defects in the binding layer so as for allow conduction of electrons through or around the binding layer) during the ECL reaction.

The electrochemiluminescent moiety can be immobilized on the particle in several ways. The electrochemiluminescent moieties may be directly attached to the immobilized assay-ligand, i.e., the binding reagent. Alternatively, the ECL moiety may be immobilized directly on the particle or a binding layer thereon, e.g., to ensure that the ECL moiety does not interfere with the activity of the assay-ligand. Such direct immobilization could be by adsorption of the unmodified ECL moiety (e.g., TAG1 adsorbs onto metals, hydrophobic surfaces, and negatively charged surfaces) or by modification of the ECL moiety with a group with a high affinity for the surface (e.g., a thiol for gold). The ECL moiety may be covalently attached to the surface, for example by the coupling of the ECL moiety comprising an activated silane to a silicon oxide or metal oxide surface or by coupling of ECL moiety to functional groups present on a plastic particle. The ECL moiety may be immobilized by attachment to a binding layer (e.g., an carboxylic acid or amine-containing label can be attached to a protein-coated microparticle by the formation of amide bonds). The ECL moiety may also be incorporated in the particle, e.g., by blending it in a plastic particle, by attaching it within the pores of a porous particle, or by enclosing it in a liposome.

In some embodiments of the invention, the ECL coreactant (or derivative thereof) is immobilized on the microparticle (e.g., by adsorption or covalent attachment). In said embodiments, the ECL moiety may be free in solution (i.e., the ECL coreactant acts as the detected label in an assay). Alternatively, the ECL moiety and the ECL coreactant are both immobilized on the microparticle so as to increase the efficiency (through forcing the ECL coreactant and ECL moiety into proximity) of reactions between the ECL moiety (or reaction products thereof) and the ECL coreactant (or reaction products thereof).

The invention is not limited in the ECL moieties and ECL coreactants that may be used and can generally be applied to any system of ECL moiety and/or coreactant. ECL moieties that may be used include: transition metal complexes (e.g., of Ru, Os, Cr, Cu, Ir, Pd, Pt, Re), polypyridyl complexes of transition metals (especially, ruthenium, osmium and rhenium), lanthanide chelates, luminol (and other chemiluminescent diacylhydrazides), luciferase, acridinium esters, polyaromatic hydrocarbons (for example, 9,10-diphenylanthracene-2-sulfonate), and such. ECL coreactants may be species that undergo oxidation or reduction at an electrode to give high energy intermediates. These intermediates react in turn react with ECL moieties (or reaction products thereof), the products of said reactions being capable of emitting light. Examples of coreactants that may be used include: amines, NADH, flavins, dansylated amines, oxalate, persulfate, peracids, hydrogen peroxide, and such. Other ECL moieties and coreactants that may be used include those disclosed in the following publications (and references cited therein): Bard, et al. (U.S. Pat. No. 5,238,808); Knight et al., 1994, Analyst, 119:879-890; U.S. Pat. No. 5,591,581; U.S. Pat. No. 5,597,910; PCT published application WO90/05296; PCT published application WO96/24690; PCT published application WO96/33411; PCT published application WO96/39534, PCT published application WO96/41175 and PCT published application WO96/40978; Watanabe, et al., *Photochemistry and Photobiology,* 1992, 55:903-909; Knight et al, *Analyst,* 1996, 121:101R-106R; Bruno et al., *J. Biolumin. Chemilumin.,* 1996, 11:193-206; Irons et al., Analyst, 1995, 120: 477-483; Knight et al., *Analyst,* 1995, 120: 1077-1082.

In one embodiment of the invention, a plurality of ECL moieties are linked to a polymer chain, wherein said polymer chain is an assay ligand or, alternatively, wherein said polymer chain is linked to an assay ligand. The polymer chain may be a linear polymer or, alternatively, a branched polymer such as a dendrimer. The polymer may contain monomer units capable of being linked to an ECL moiety or an assay ligand (e.g., thiols, aldehydes, carboxylic acids or activated derivatives thereof, amines, disulfides, alcohols, and such). Alternatively, the ECL moiety and/or assay ligand are linked to a monomer that is incorporated into a polymer during the course of a polymerization reaction.

The attachment of chemical groups (including biological molecules) to polymers by the modification of preformed polymers, and/or by the incorporation of modified monomers into a growing polymer, is well known. The types of polymers that may be used include, but are not limited to, polymers or copolymers containing the following classes of monomeric units: vinyl units (e.g., ethylene, propylene, acrylonitrile, acrylates, acrylamides, styrene, vinylacetate, maleic anhydride), amino acids, amino alcohols, silanes, epoxides, diamines, aldehydes, ketones, and such. The polymers may comprise polypeptides (e.g., proteins), polynucleotides, and/or analogs thereof. By way of example, a polymer presenting amine groups (e.g., polylysine) can be modified with an assay ligand, (e.g. a biotin moiety) and with a plurality of ECL moieties by reaction of the polymer with the NHS ester of biotin (or a derivative thereof) and the NHS ester of an ECL moiety (e.g., TAG1). In another example, acrylamide monomers with the structures $CH_2CHCONH_2$, $CH_2CHCONH$-L-BT, and $CH_2CHCONH$-L-TAG (wherein, L is a linking moiety, BT is biotin, and TAG is an ECL moiety) are copolymerized to form a copolymer presenting a biotin moiety and a plurality of ECL moieties. We have found that when such polymers bind to streptavidin molecules located on an electrode support and we excite ECL from the ECL moieties, the ECL intensity increases with increasing number of ECL moieties per polymer chain. When comparing polymer chains bearing different numbers of ECL moieties, the ECL intensity of the streptavidin-bound polymers was roughly proportional to the surface photoluminescence. This result shows that we can efficiently induce all the ECL moieties to electrochemiluminesce even on heavily labeled polymer chains.

The polymers of the invention may take the form of microparticles. For example, a polymeric microparticle may be linked to one or more members of the following group: i) a plurality of ECL moieties, ii) a plurality of ECL coreactants, and/or iii) one or more assay ligands. These species may be located on the surface of the particle or within the interior. For example, a microparticle may be formed by suspension polymerization (e.g., of a crosslinked polymer). Microparticles linked to ECL moieties, ECL coreactants, and/or assay ligands may be formed by including in the polymerization reaction monomer units linked to ECL moieties, ECL coreactants, and/or assay ligands. Alternatively, one or more of these species may be attached to the fully polymerized microparticles. In one embodiment of the invention, the microparticle is porous so as to allow the diffusion of reactive species into the particles (e.g., to allow the diffusion of ECL coreactants to ECL moieties within the particle). In another embodiment of the reaction, the microparticle is made of a conducting polymer (e.g., polypyrrole, polyaniline, polythiophene, or polyacetylene) so as to ensure efficient oxidation or reduction of electroactive species (e.g., ECL moieties and/or coreactants) throughout the particle.

Assays of the Invention Using Microparticles

Assays Using Microparticles Comprising ECL Moieties

The assays for an analyte-of-interest in a sample comprise the steps of (a) forming a composition comprising (i) a sample, (ii) a microparticle having one or more copies of a first assay-ligand immobilized on its surface and a plurality of ECL moieties immobilized on its surface (iii) a second assay-ligand immobilized on an electrode; (b) incubating the composition to form a complex; and (c) conducting an ECL measurement in the presence of ECL reactants. Said first and second assay-ligands may be the same or different. A complex is thus formed including (i) a microparticle having one or more copies of an assay-ligand immobilized on its surface, and a plurality of copies of an ECL moiety immobilized on its surface, and (ii) an assay-ligand immobilized on an electrode.

The formation of said composition comprising said sample, said microparticle, and said second assay-ligand may be one step or may be further subdivided into a plurality of steps. For example, the sample and the microparticle may be combined and incubated to form a complex that is then contacted with the second assay-ligand immobilized on an electrode. Alternatively, said sample and said second assay-ligand immobilized on an electrode may be combined to form a complex on the electrode that is then contacted with said microparticle.

In an alternate embodiment, the second assay-ligand is immobilized on a solid-phase support other than an electrode, said solid-phase support being capable of being collected at (or bought into contact with) an electrode. Assays of this alternate embodiment comprise the steps of (a) forming a composition comprising (i) a sample, (ii) a microparticle having one or more copies of a first assay-ligand immobilized on its surface and a plurality of ECL moieties immobilized on its surface (iii) a second assay-ligand immobilized on a solid phase support; (b) collecting said solid-phase support at (or bringing said solid phase support into contact with) an electrode; and (c) conducting an ECL measurement in the presence of ECL reactants. Said first and second assay-ligands may be the same or different. A complex is thus formed including (i) a microparticle having one or more copies of an assay-ligand immobilized on its surface, and a plurality of copies of an ECL moiety immobilized on its surface, and (ii) an assay-ligand immobilized on an solid-phase support. Suitable apparatus and solid-phase supports (e.g., magnetic beads) for carrying out assays according to this embodiment include those disclosed in PCT published application WO92/14139 and PCT published application WO90/05301.

The methods and compositions of the invention may be constructed in a wide variety of formats. Such formats include formats known in the art such as sandwich assays and competitive binding assays (see, e.g., the following references, hereby incorporated by reference: *Nonradioactive Labeling and Detection of Molecules*, Kessler, C., ed., Springer-Verlag: Berlin 1992; *The Immunoassay Handbook*, Wild, D., ed., Stackton Press: New York 1994; and Keller, G. H.; Manak, M. M. *DNA Probes*, 2nd Ed., MacMillan Publishers Ltd.: London, 1993; *Tietz Textbook of Clinical Chemistry* $2^{nd}$ *Edition*, Burtis et al. Ed., W.B. Saunders and Co.: Philadelphia, 1994). For example, a sandwich assay may be performed so that a complex is formed including (i) a microparticle having one or more copies of a first assay-ligand immobilized on its surface, and a plurality of copies of an ECL moiety immobilized on its surface, (ii) a second assay-ligand immobilized on an electrode (and/or solid-phase support), and (iii) an analyte, wherein said analyte is bound to both said first assay-ligand and said second assay-ligand so as to link said microparticle to said electrode (and/or solid-phase support). In another example, a competitive binding assay may be performed so that a complex is formed including (i) a microparticle having one or more copies of a first assay-ligand immobilized on its outer surface, and a plurality of copies of an ECL moiety immobilized on its surface, and (ii) a second assay-ligand immobilized on an electrode (and/or solid-phase support), wherein said first assay-ligand is the analyte (or an analog thereof), said second assay-ligand is a binding partner of said analyte, and said first and second assay-ligand are bound to each other so as to link said microparticle to said electrode (and/or solid-phase support). Typically, in competitive binding assays, the presence of the analyte of interest in a sample results in a decrease in the number of said complexes and, therefore, in the ECL signal. In an alternate embodiment of said competitive binding assay, said second assay-ligand is the analyte (or an analog thereof) and said first assay-ligand is a binding partner of said analyte.

As described above, some assays of the invention use a microparticle having one or more copies of an assay-ligand immobilized on its surface and a plurality of ECL moieties immobilized on its surface (i.e., the microparticle having a plurality of ECL moieties immobilized on its surface is used as a label for the assay-ligand). We have found that the use of said particles gives an enhancement in the signal observed in an ECL binding assay for an analyte-of-interest. This enhancement occurs because microparticles can be used that have many more ECL moieties than can typically be put on an assay-ligand by direct attachment (and; therefore, more ECL moieties can be induced to electrochemiluminescence per binding event of the assay). For example, a labeled nucleic acid probe used in an ECL nucleic acid hybridization assay typically has one ECL moiety per probe molecule; a labeled antibody used in an ECL immunoassay will typically have 1-10 ECL moieties per antibody. We have prepared microparticles having more than 100 labels per particle. A rough estimate of the numbers of ECL-moieties that can be put on a solid particle can be determined from the ratio of the surface area of the particle to the cross-sectional area of the labeling reagent. The number of ECL moieties may be even higher if the ECL moieties are incorporated within the volume of the microparticle or a coating thereon.

Assays Using Microparticles Comprised of an Electrically Conductive

Material and Comprising ECL Moieties

The assays for an analyte-of-interest in a sample comprise the steps of (a) forming a composition comprising (i) a sample, (ii) microparticles comprised of an electrically conductive material having one or more copies of a first assay-ligand immobilized on its surface and a plurality of ECL moieties immobilized on its surface (iii) a second assay-ligand immobilized on an electrode; (b) incubating the composition to form a complex; and (c) conducting an ECL measurement in the presence of ECL reactants. Said first and second assay-ligands may be the same or different in structure and/or specificity. A complex is thus formed including (i) microparticles comprised of an electrically conductive material having one or more copies of a first assay-ligand immobilized on its outer surface, and a plurality of copies of an ECL moiety immobilized on its surface, and (ii) a second assay-ligand immobilized on an electrode.

The formation of said composition comprising said sample, said microparticle comprised of an electrically conductive material, and said second assay-ligand may be one step or may be further subdivided into a plurality of steps. For example, the sample and the microparticle may be combined and incubated to form a complex that is then contacted with the second assay-ligand immobilized on an electrode. Alternatively, said sample and said second assay-ligand immobilized on an electrode may be combined to form a complex on the electrode that is then contacted with said microparticle.

In an alternate embodiment, the second assay-ligand is immobilized on a solid-phase support other than an electrode, said solid-phase support being capable of being collected at (or being brought into contact with) an electrode. Assays of this alternate embodiment comprise the steps of (a) forming a composition comprising (i) a sample, (ii) microparticles comprised of an electrically conductive material having one or more copies of a first assay-ligand immobilized on its surface and a plurality of ECL moieties immobilized on its surface (iii) a second assay-ligand immobilized on a solid phase support; (b) collecting said solid-phase support at (or bringing said solid-phase support into contact with) an electrode; and (c) conducting an ECL measurement in the presence of ECL reactants. Suitable apparatus and solid-phase supports (e.g., magnetic beads) for carrying out assays according to this embodiment include those disclosed in PCT published application WO92/14139 and PCT published application WO90/05301.

The methods and compositions of the invention may be constructed in a wide variety of formats. Such formats include formats known in the art such as sandwich assays and competitive binding assays (see, e.g., the following references, hereby incorporated by reference: *Nonradioactive Labeling and Detection of Molecules*, Kessler, C., ed., Springer-Verlag: Berlin 1992; *The Immunoassay Handbook*, Wild, D., ed., Stackton Press: New York 1994; and Keller, G.

H.; Manak, M. M. *DNA Probes,* 2nd Ed., MacMillan Publishers Ltd.: London, 1993; *Tietz Textbook of Clinical Chemistry 2nd Edition,* Burtis et al. Ed., W.B. Saunders and Co.: Philadelphia, 1994). For example, a sandwich assay for an analyte of interest may be performed so that a complex is formed including (i) a microparticle comprised of an electrically conductive material and having one or more copies of a first assay-ligand immobilized on its surface, and a plurality of copies of an ECL moiety immobilized on its surface, (ii) a second assay-ligand immobilized on an electrode (and/or solid-phase support), and (iii) an analyte, wherein said analyte is bound to both said first assay-ligand and said second assay-ligand so as to link said microparticle to said electrode (and/or solid-phase support). In another example, a competitive binding assay for an analyte of interest may be performed so that a complex is formed including (i) a microparticle comprised of an electrically conductive material and having one or more copies of a first assay-ligand immobilized on its outer surface, and a plurality of copies of an ECL moiety immobilized on its surface, and (ii) a second assay-ligand immobilized on an electrode (and/or solid-phase support), wherein said first assay-ligand is the analyte (or an analog thereof), said second assay-ligand is a binding partner of said analyte, and said first and second assay-ligand are bound to each other so as to link said microparticle to said electrode (and/or solid-phase support). Typically, in competitive binding assays, the presence of the analyte of interest in a sample results in a decrease in the number of said complexes and, therefore, in the ECL signal. In an alternate embodiment of said competitive binding assay, said second assay-ligand is the analyte (or an analog thereof) and said first assay-ligand is a binding partner of said analyte.

As described above, some assays of the invention use a microparticles comprised of a conductive material and having one or more copies of an assay-ligand immobilized on its surface and a plurality of ECL moieties immobilized on its surface (i.e., the microparticles comprised of a conductive material and having a plurality of ECL moieties immobilized on its surface is used as a label for the assay-ligand). We have found that the use of said particles gives an enhancement in the signal observed in an ECL binding assay for an analyte-of-interest. This enhancement occurs because microparticles can be used that have many more ECL moieties than can typically be put on an assay-ligand by direct attachment (and, therefore, more ECL moieties can be induced to electrochemiluminescence per binding event of the assay). For example, a labeled nucleic acid probe used in an ECL nucleic acid hybridization assay typically has one ECL moiety per probe molecule; a labeled antibody used in an ECL immunoassay will typically have 1-10 ECL moieties per antibody. We have prepared microparticles having more than 100 labels per particle. A rough estimate of the numbers of ECL-moieties that can be put on a solid particle can be determined from the ratio of the surface area of the particle to the cross-sectional area of the labeling reagent. The number of ECL moieties may be even higher if the ECL moieties are incorporated within the volume of the microparticle or a coating thereon.

The use of microparticles comprised of conductive materials can lead to additional enhancements in ECL signal when compared to microparticles comprised of non-conductive materials. Without being bound by theory, it is believed that this additional enhancement is due to the ability of the microparticle itself to act as an electrode for oxidizing and/or reducing ECL moieties on its surface. The size of a microparticle having a plurality of ECL moieties immobilized thereon may prevent some of said moieties from coming into close enough proximity to a working electrode to be oxidized and/or reduced directly by the electrode. It is believed that these proximity limitations are overcome by the use of microparticles comprised of conductive materials because the microparticle can carry electrical energy from the working electrode to said ECL moieties and/or can act as a working electrode to oxidize and/or reduce said ECL moieties (as well as additional ECL moieties, reactants or cofactors in solution).

FIG. 1 is an illustration of one embodiment of the invention. The figure illustrates a "sandwich" immunoassay using a microparticle (101) comprised of a conductive material and coated with a TAG-labeled antibody (102). The assay for an analyte-of-interest (103) in a sample comprises the steps of (a) forming a composition comprising (i) a sample including an unknown concentration of the analyte-of-interest (103), (ii) a microparticle (101) comprised of a conductive material and having a plurality of TAG-labeled first antibodies immobilized on said microparticle, wherein said first antibodies (102) are capable of binding said analyte-of-interest (103), and (iii) a second antibody (104) immobilized on a working electrode (105), wherein said second antibody (104) is capable of binding said analyte-of-interest (103); (b) incubating said composition to form a complex; and (c) conducting an ECL measurement in the presence of ECL reactants, wherein luminescence (106) is generated.

Assays Using Microparticles Comprised of an Electrically Conductive Material

The assays for an analyte-of-interest in a sample comprise the steps of (a) forming a composition comprising (i) a sample, (ii) a microparticle comprised of an electrically conductive material having one or more copies of a first assay-ligand immobilized on its surface (iii) a second assay-ligand immobilized on an electrode; (b) incubating the composition to form a complex; and (c) conducting an ECL measurement in the presence of ECL reactants. Said first and second assay-ligands may be the same or different. A complex is thus formed including (i) a microparticle having one or more copies of an assay-ligand immobilized on its outer surface, and (ii) an assay-ligand immobilized on an electrode.

The formation of said composition comprising said sample, said microparticle comprising electrically conductive material, and said second assay-ligand may be one step or may be further subdivided into a plurality of steps. For example, the sample and said microparticle may be combined and incubated to form a complex that is then contacted with the second assay-ligand immobilized on an electrode. Alternatively, said sample and said second assay-ligand immobilized on an electrode may be combined to form a complex on the electrode that is then contacted with said microparticle.

In an alternate embodiment, the second assay-ligand is immobilized on a solid-phase support other than an electrode, said solid-phase support being capable of being collected at (or brought into contact with) an electrode. Assays of this alternate embodiment comprise the steps of (a) forming a composition comprising (i) a sample, (ii) a microparticle having one or more copies of a first assay-ligand immobilized on its surface and a plurality of ECL moieties immobilized on its surface (iii) a second assay-ligand immobilized on a solid phase support; (b) collecting said solid-phase support at (or bringing said solid phase support into contact with) an electrode; and (c) conducting an ECL measurement in the presence of ECL reactants. Suitable apparatus and solid-phase supports (e.g., magnetic beads) for carrying out assays according to this embodiment include those disclosed in PCT published application WO92/14139 and PCT published application WO90/05301.

The methods and compositions of the invention may be constructed in a wide variety of formats. Such formats include formats known in the art such as sandwich assays and competitive binding assays (see, e.g., the following references, hereby incorporated by reference: *Nonradioactive Labeling and Detection of Molecules*, Kessler, C., ed., Springer-Verlag: Berlin 1992; *The Immunoassay Handbook*, Wild, D., ed., Stackton Press: New York 1994; and Keller, G. H.; Manak, M. M. *DNA Probes*, 2nd Ed., MacMillan Publishers Ltd.: London, 1993; *Tietz Textbook of Clinical Chemistry $2^{nd}$ Edition*, Burtis et al. Ed., W.B. Saunders and Co.: Philadelphia, 1994). For example, a sandwich assay may be performed so that a complex is formed including (i) a microparticle comprised of an electrically conductive material and having one or more copies of a first assay-ligand immobilized on its surface, (ii) a second assay-ligand immobilized on an electrode (and/or solid-phase support), and (iii) an analyte, wherein said analyte is bound to both said first assay-ligand and said second assay-ligand so as to link said microparticle to said electrode (and/or solid-phase support). In another example, a competitive binding assay may be performed so that a complex is formed including (i) a microparticle comprised of an electrically conductive material and having one or more copies of a first assay-ligand immobilized on its surface, and (ii) a second assay-ligand immobilized on an electrode (and/or solid-phase support), wherein said first assay-ligand is the analyte (or an analog thereof), said second assay-ligand is a binding partner of said analyte, and said first and second assay-ligand are bound to each other so as to link said microparticle to said electrode (and/or solid-phase support). Typically, in competitive binding assays, the presence of the analyte of interest in a sample results in a decrease in the number of said complexes and, therefore, in the ECL signal. In an alternate embodiment of said competitive binding assay, said second assay-ligand is the analyte (or an analog thereof) and said first assay-ligand is a binding partner of said analyte.

As described above, some assays of the invention use a microparticle comprised of a conductive material and having one or more copies of an assay-ligand). In assays using said microparticles, the ECL signal may be generated from ECL moieties in solution (as opposed to ECL moieties immobilized on said microparticles), said microparticles acting to modulate the ECL generated at a working electrode. Advantageously, the working electrode is comprised of an electrode material that is inactive or only weakly active for generating ECL from a particular ECL moiety and/or ECL coreactant ("ECL-inactive"). Some examples of electrode materials that may, under certain conditions, be ECL-inactive for generating ECL from TAG1 in the presence of tripropylamine include nickel and some compositions of stainless steel. In addition, some metals (such as gold) and graphitic materials become less ECL active (under certain conditions) after electrochemical oxidation at high oxidation potentials.

Advantageously, the microparticle is comprised of an ECL-active material. Some examples of materials that are ECL-active include gold, platinum, carbon and tin oxide (said tin oxide preferably doped with indium or antimony), and polythiophene. Additional ECL-active and ECL-inactive systems can be determined by testing electrodes for their ability to generate ECL from specific systems of ECL labels and coreactants. The formation of a complex including i) a microparticle comprised of ECL-active material and having one or more copies of an assay-ligand immobilized on its surface and (ii) an assay-ligand immobilized on an electrode comprised of an ECL-inactive but conducting material, will enable ECL to be induced from ECL moieties in solution. The formation of said complex is, therefore, detected as a modulation in the ability of the electrode to induce ECL from ECL moieties in solution. The advantage of this embodiment is that the ECL moieties are in solution so the number of ECL moieties that can be induced to emit ECL is not limited by the number of moieties that can be immobilized in or on a particle of a given size. A high degree of amplification can be achieved by using high concentrations of ECL moieties in solution so that many ECL moieties are induced to emit ECL.

Figure 2:
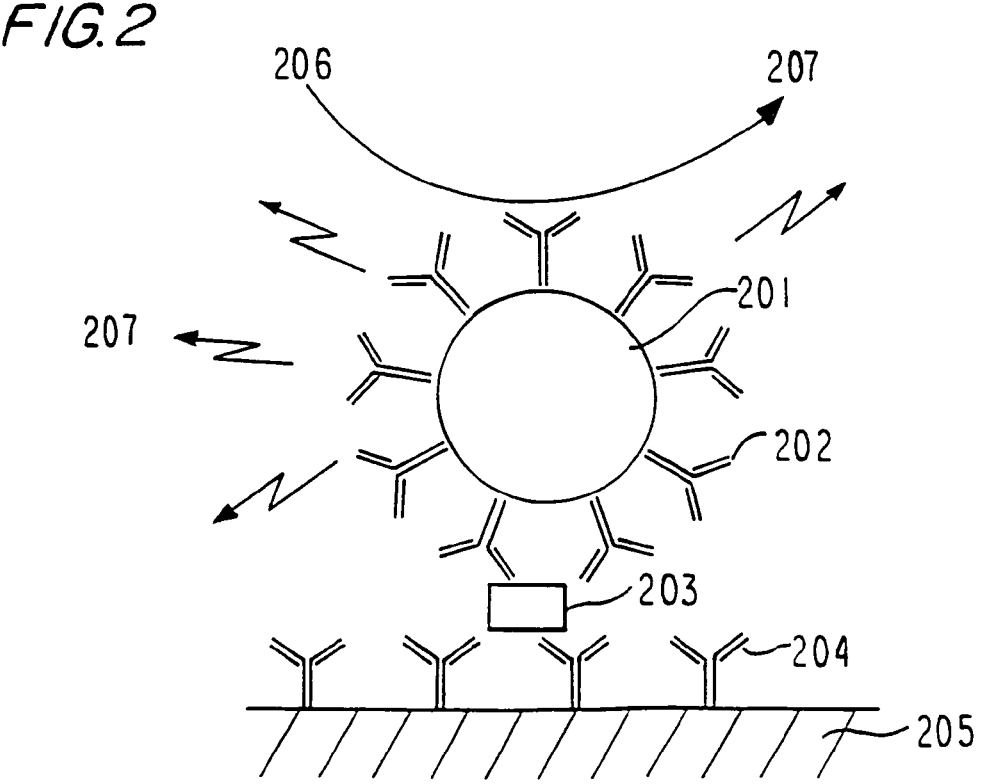
FIG. 2 is a schematic representation of another embodiment of the invention employing a microparticle of the invention having antibody immobilized upon it and a sandwich immunoassay using that particle in an electrochemiluminescence assay using free ECL moieties in solution.

FIG. 2 is an illustration of one embodiment of the invention. The figure illustrates a complex including i) a microparticle (201) comprised of an ECL-active material and having an antibody (202) immobilized thereon, wherein said first antibody (202) is capable of binding an analyte-of-interest (203); ii) an antibody (204) immobilized on an electrode (205) comprised of an ECL-inactive material, wherein said antibody (204) is capable of binding said analyte-of-interest (203) and iii) said analyte-of-interest (203). The electrode itself (205) is not capable of causing ECL from ECL moieties (206) in solution, however, the ECL-active particle (201) is capable of carrying electrical energy from the electrode and/or of acting as an electrode so as to induce ECL (207) from ECL moieties (206) in solution.

EXAMPLES

Instrumentation, Materials, and Methods (1) Materials.

PBS-1 (100 mM sodium phosphate, 150 mM sodium chloride, pH 7.8), Assay Buffer (ORIGEN Assay Buffer, a buffered solution containing triproylamine and detergent), and TAG1-NHS (a NHS ester-containing derivative of ruthenium tris-bipyridyl) are all products of IGEN International. Succinimidyl-4-(N-maleimidomethyl)-cyclohexane-1-carboxylate (SMCC) was purchased from Pierce Chemical. Co. Antibody Diluent (Elecsys AFP Antibody Diluent, Boehringer-Mannheim) is a mixture of blocking agents suitable for conducting AFP assays. Calibration solutions containing known amounts of AFP were prepared in Calibrator Diluent (Elecsys AFP Calibrator Diluent, Boehringer-Mannheim), an artificial serum substitute.

Sandwich immunoassays for AFP were conducted using an antibody pair purchased from Genzyme (Cat. #MMA1010). The capture antibody (Antibody #2) was labeled with biotin by reacting the antibody (1 mg, 6.7 nmol, in 180 uL of 15 mM phosphate, pH 7.4) with 40 ug (72 nmol) of biotin-LC-sulfo-NHS ester (IGEN International). The biotin-labeled antibody was purified by gel filtration and diluted in Antibody Diluent to a concentration of 7.5 ug/mL. The detection antibody (Antibody #1) was labeled with TAG1 by reacting the antibody (at a concentration of >1 mg/mL in 15 mM phosphate, pH 7.4) with TAG1-NHS (at a concentration of 10 mg·mL in 2.2 uL DMSO). The TAG1-labeled antibody was purified by gel filtration using 5 mM borate, pH 8.8 as the eluent. The number of labels per protein was determined by measuring the concentration of TAG1 moieties (by optical absorption) and the concentration of protein (BCA Assay, Pierce Chemical Co.).

Composite electrodes containing 27% (w/w) Hyperion. Fibrils in co-ethylene-co-vinyl acetate (EVA) according to the procedure of PCT application US 97/16942. In brief, the materials were compounded and then extruded into sheets of flexible material that could be stamped or cut to form EVA-fibril composite electrodes. PCT application US 97/16942 also describes the procedure for coating the EVA-fibril composite with an immobilized layer of streptavidin. In brief, the procedure was as follows: i) oxidation of the EVA-fibril composite (for 20 min. in a mixture containing 20.7 g of chromium trioxide, 30 mL of water, and 10 mL of concentrated sulfuric acid); ii) treatment of the surface with 0.7 g of N-hydroxysuccinimide (NHS) and 1.6 g of 1-ethyl-3-dimethylaminopropyl-carbodiimide (EDC) in 50 mL of methylene chloride to form NHS esters and iii) treatment of the surface with a solution of streptavidin (5 mg in 50 mL of PBS-1) for 4 h to immobilize streptavidin on the composite. The chromic acid oxidation was sometimes replaced by treatment of the composite with an oxygen plasma (Advanced Plasma Systems Series C Reactor, 2000 W, 10 min., 300 mtorr) with similar results.

(2) ECL Measurements

ECL was measured in electrochemical cells designed to hold 3/16" or 5/16" discs of the composite material (working electrode). The electrode was sealed (with an o-ring) against an aperture to form one surface of the cell. The cell also included counter and reference electrodes. Light emitted from the working electrode surface was measured with a photomultiplier tube (PMT). The potential at the working electrode was controlled with a potentiostat.

In a typical ECL experiment, the cell was filled with Assay Buffer and the potential at the working electrode was ramped from 0 V to −0.8V to 2.3 V at a scan rate of 0.1 V/s. The peak ECL signal occurred typically at about 1.0 V. We report the integrated photocurrent measured at the PMT in units of nA's. We note that the signal is dependent on the gain of the PMT so data shown for different experiments is not necessarily directly comparable.

Binding reactions on the composite electrode surfaces were sometimes carried out in the ECL cell. In other cases, we carried out the binding reactions in a separate container then transferred the composite electrodes to the ECL cell for the measurement of ECL.

Example I

Synthesis of Gold Colloids with a Diameter of ~40 nm

The colloids were prepared by the procedure of G. Frens (Nature Phys. Sci. 1973, 241, 20-22). A solution of $HAuCl_4$ (0.01% by weight, 200 mL) was heated to boiling in a glass beaker covered with a crystallization dish. A solution of sodium citrate (1% by weight, 2.0 mL) was then added. The combined solutions were allowed to boil for another 10 min. and then allowed to cool to room temperature. The resulting colloidal suspension had a dark red color. The suspension was stored at 4° C. until used.

Example II

Procedure for Coating Gold Colloids with TAG1-Labeled Antibody

The stock suspension of colloidal gold (10.9 mL) was adjusted to ~pH 8.8 by the addition of 65 uL of 0.1 M potassium carbonate. TAG1-labeled antibody (83.3 uL of a 1.2 mg/mL solution in 5 mM sodium borate, pH 8.8) was added with mixing to give a final concentration of protein of 10 ug/mL. The adsorption was allowed to proceed for 45 min at room temp. Polyethylene glycol (PEG) was added (1 mL of a 1% w/v solution) as a stabilizer. Centrifugation (270×g, 20 min) removed aggregated particles. The colloidal particles were centrifuged to a pellet (17,000×g, 1 h) then resuspended in 5 mM sodium borate, 0.1% PEG, pH 8.8. This process was repeated two more times to ensure removal of excess non-adsorbed protein. Prior to its use in an AFP assay, the antibody-coated gold colloid was first diluted in Antibody Diluent to, a concentration of 1.2 ug of gold-bound antibody per mL of solution.

Example III

Procedure for Coating Colloidal Particles of Silica or Titanium Dioxide with TAG1-Labeled Antibody Colloidal silica particles with an average diameter of 40 nm (Aerosil OX50, Degussa Corp.) were coated with TAG1-labeled anti-AFP antibody by the procedure given below. Colloidal titanium dioxide (Titanium Dioxide P25, Degussa Corp.) was coated by an analogous procedure. A suspension containing the silica at a concentration of 1 mg/mL in 5 mM borate, pH 8.9 was sonified (Sonifier 250, Branson Ultrasonics), for 20 min. The suspension was further diluted in the borate buffer to give a concentration of silica of 30 ug/mL. TAG1-labeled anti-AFP antibody was added to 5 mL of the suspension to give a concentration of 30 ug/mL and the suspension was incubated for 0.45 min. at room temperature. Polyethylene glycol (PEG) was added (0.5 mL of a 1% w/v solution) as a stabilizer. The colloidal particles were centrifuged to a pellet (15,000×g, 45 min.) then resuspended in 5 mM sodium borate, 0.1% PEG, pH 8.9. This process was repeated two more times to ensure removal of excess non-adsorbed protein. Prior to its use in AFP assay, the antibody-coated silica was first diluted in Antibody Diluent to a coated silica was first diluted in Antibody Diluent to a concentration of 1.2 ug of gold-bound antibody per mL of solution.

Example IV

Procedure for Immobilizing Antibody and TAG1 on BSA-Coated Colloidal Gold

The stock suspension of colloidal gold (11 mL) was adjusted to ~pH 8.8 by the addition of 77 uL of 0.1 M potassium carbonate. Bovine serum albumin (BSA) was added (1.22 mL of a 10 mg/mL solution in 5 mM sodium borate, pH 8.8) with mixing to give a final concentration of protein of 10 ug/mL. The adsorption was allowed to proceed for 2 hr at room temp. The colloidal particles were washed three times by centrifugation and resuspension in 5 mM sodium borate, 0.02% Triton X-100, pH 8.8, the final resuspension being in 4 mL of PBS-Triton (15 mM sodium phosphate, 150 mM sodium chloride, pH 7.2). An aliquot of the suspension (200 uL) was then treated with TAG1 NHS (10 uL of a 320 uM solution in DMSO) and SMCC (10 uL of a 3200 uM solution in DMSO) to couple, respectively, TAG1 and maleimide groups to the BSA layer. The reaction was allowed to proceed for 2 hrs then the particles were washed two times with PBS-Triton and resuspended in 100 uL of PBS-Triton-EDTA (PBS-Triton containing EDTA at a concentration of 1 mM).

The thiol-reactive maleimide groups were used to immobilized anti-AFP antibodies on the surface. The antibody (Boehringer-Mannheim) had been treated prior to the immobilization with a 17 fold excess of Traut's Reagent t introduce thiol groups and had been purified by gel filtration chromatography. The thiolated antibody (100 uL of a 0.5 mg./mL solution in PBS-Triton-EDTA) was combined with the colloidal suspension and the reaction was allowed to proceed overnight. Cysteine, BSA and glycerol were added (to give final concentrations of 1 mM, 1 mg/mL, and 10%, respectively) and the particles were washed three times by centrifugation and resuspension in a solution containing 15 mM phosphate, 150 mM sodium chloride, 1 mg/mL BSA and 10% (w/v) glycerol. After the last wash, the particles were resuspended in 100 uL of the wash buffer. The suspension was diluted 1:5 in Antibody Diluent before use in an AFP assay.

Example V

AFP Assay Using Colloidal Gold Coated with TAG1-Labeled Anti-AFP Antibody

The assay procedure was as follows: The streptavidin-coated electrodes (3/16" diameter discs) were treated with 100 uL of biotin-labeled antibody. The binding of the capture antibody was allowed to proceed for 1 h with gentle shaking, then the electrodes were washed twice with PBS (150 uL). The electrodes were then treated with a mixture containing 105 uL of the suspension of antibody-coated gold colloid (prepared as described in Example II, ~1.5 TAGs per protein) and 20 uL of a solution containing a known quantity of AFP dissolved in Calibrator Diluent. The assay was allowed to proceed for 1 h with gentle shaking. The electrodes were then washed with PBS (2×150 uL) and stored in 50 mM phosphate, pH 7.5 containing 1% BSA. The electrodes were placed in the ECL cell and ECL was then measured in the presence of ECL Assay Buffer (IGEN International, Inc.)

Figure 3:
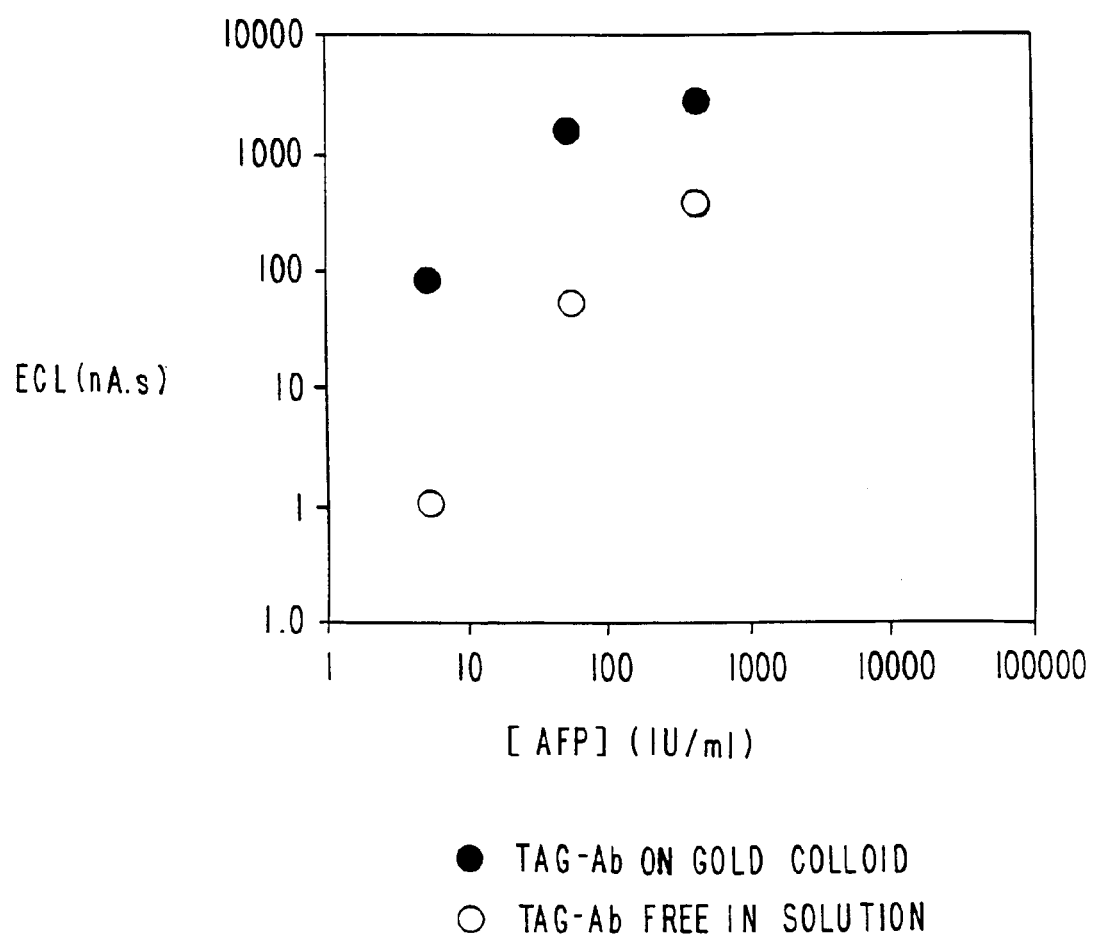
FIG. 3 is a plot of the ECL signal (background corrected) measured in an ECL sandwich immunoassay for AFP as a function of the concentration of AFP in the sample, wherein the secondary antibody was labeled with TAG 1 and coated on the surface of colloidal gold particles. The ECL signal obtained when the TAG 1 labeled antibody was not linked to a microparticle is also given for comparison.

FIG. 3 gives the ECL signal minus the ECL background as a function of the concentration of AFP in the sample (the background is the ECL signal when no AFP was present in the sample). For comparison, data is shown for the analogous assay using free TAG1-labeled anti-AFP antibody in solution (as opposed to antibody adsorbed on a colloid). The total concentration of antibody in the assay using colloid-adsorbed TAG1-labeled antibody was the same as the assay using free TAG1-labeled antibody. The results clearly show a dramatic increase in the signal minus background for the lower concentrations of AFP. We also note that the antibody-coated gold colloid exhibited low levels of non-specific binding; the background signal observed for the antibody-coated gold reagent was slightly lower than that observed for the free TAG1-labeled antibody in solution.

Example VI

AFP Assay Using Colloidal Silica Coated with TAG1-Labeled Anti-AFP Antibody

The assay procedure was as follows: The streptavidin-coated electrodes (3/16" or 5/15" diameter discs) were treated with 100 uL of biotin-labeled antibody. The binding of the capture antibody was allowed to proceed for 1 h with gentle shaking, then the electrodes were washed twice with PBS (150 uL). The electrodes were then treated with a mixture containing 100 uL of the suspension of antibody-coated silica colloid (prepared as described in Example III, ~2.7 TAGs per protein) and 20 uL of a solution containing a known quantity of AFP dissolved in Calibrator Diluent. The assay was allowed to proceed for 1 h with gentle shaking. The electrodes were then washed with PBS (2×150 uL) and stored in 50 mM phosphate, pH 7.5 containing 1% BSA. The electrodes were placed in the ECL cell and ECL was then measured in the presence of Assay Buffer (IGEN International, Inc.).

The table below gives the ECL signal measured for a sample (containing AFP at a concentration of 5.6 IU/mL) minus the ECL background as a function of the concentration of AFP in the sample (the background is the ECL signal when no AFP was present in the sample). For comparison, data is shown for the analogous assay using free TAG1-labeled anti-AFP antibody in solution (as opposed to antibody adsorbed on a colloid) or TAG1-labeled anti-AFP adsorbed on colloidal gold particles. The total concentration of antibody was the same in each case. The results show that the ECL signal measured using the colloidal silica reagent was higher than that observed for the free antibody in solution but lower than that observed when using the colloidal gold reagent. The background signals due to the three reagents were roughly comparable.

| Labeled Reagent | Signal - Background |
| --- | --- |
| Free TAG1-Ab | 2 |
| TAG1-Ab on Gold | 91 |
| TAG1-Ab on Silica | 8 |

Example VII

Figure 4:
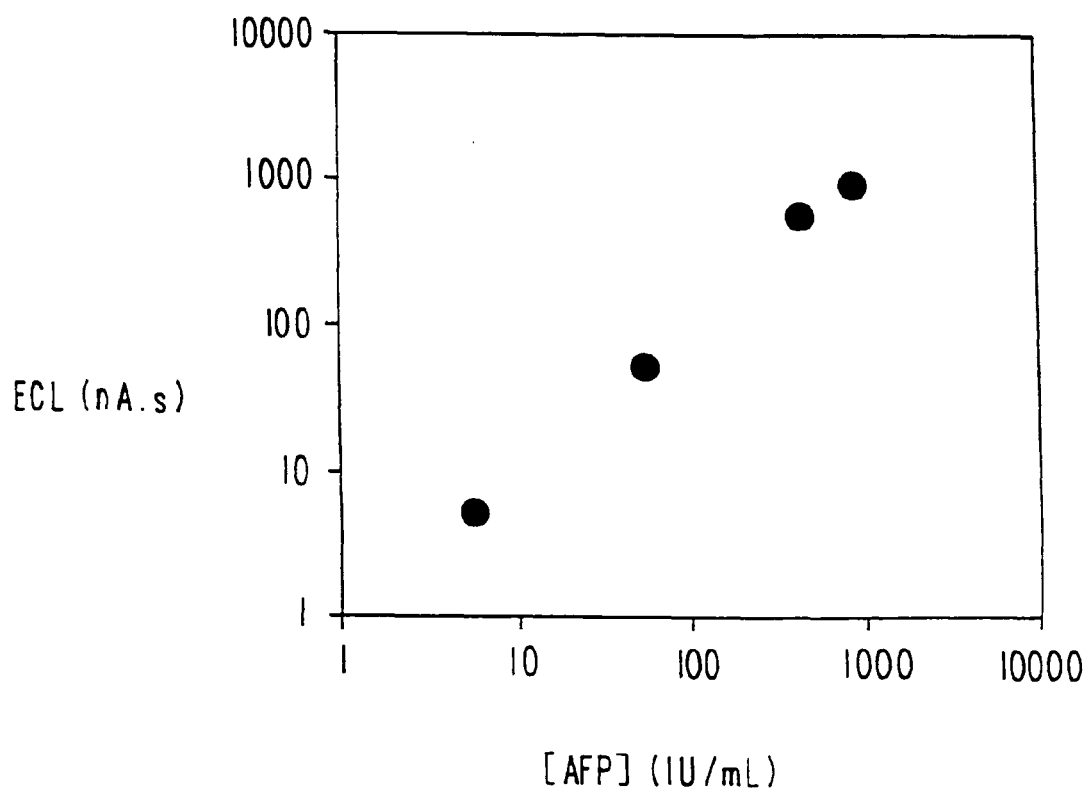
FIG. 4 is the ECL signal (background corrected) measured in an ECL sandwich immunoassay for AFP as a function of the concentration of AFP in the sample, wherein the secondary antibody was labeled with TAG1 and coated on the surface of colloidal titanium oxide particles.

AFP Assay Using Colloidal Titanium Dioxide Coated with TAG1-Labeled Anti-AFP Antibody The assay procedure was as follows: The streptavidin-coated electrodes (3/16" or 5/15" diameter discs) were treated with 100 uL of biotin-labeled antibody. The binding of the capture antibody was allowed to proceed for 1 h with gentle shaking, then the electrodes were washed twice with PBS (150 uL). The electrodes were then treated with a mixture containing 100 uL of the suspension of the antibody-coated titanium dioxide colloid (prepared as described in Example III, ~1.5 TAGs per protein) and 20 uL of a solution containing a known quantity of AFP dissolved in Calibrator Diluent. The assay was allowed to proceed for 1 h with gentle shaking. The electrodes were then washed with PBS (2×150 uL) and stored in 50 mM phosphate, pH 7.5 containing 1% BSA. The electrodes were placed in the ECL cell and ECL was then measured in the presence of ECL Assay Buffer (IGEN International, Inc.) FIG. 4 gives the ECL signal minus the ECL background as a function of the concentration of AFP in the sample (the background is the ECL signal when no AFP was present).

Example VIII

AFP Assay Using Antibody and TAG1 Immobilized on BSA-Coated Gold Colloids

The assay procedure was follows: The streptavidin-coated electrodes (3/16" or 5/15" diameter discs) were treated with 100 uL of biotin-labeled antibody. The binding of the capture antibody was allowed to proceed for 1 h with gentle shaking, then the electrodes were washed twice with PBS (150 uL). The electrodes were then treated with a mixture containing 100 uL of the colloidal reagent (prepared as described in Example IV) and 20 uL of a solution containing a known quantity of AFP dissolved in Calibrator. Diluent. The assay was allowed to proceed for 1 h with gentle shaking. The electrodes were then washed with PBS (2×150 uL) and stored in 50 mM phosphate, pH 7.5 containing 1% BSA. The electrodes were placed in the ECL cell and ECL was then measured in the presence of Assay Buffer (IGEN International, Inc.). The signal obtained for a sample containing 56 IU/mL AFP was 472 nA·s compared to a background signal of 121 nA·s.

Example IX

The Use of Polymers Linked to a Plurality of ECL Moieties as Labels for ECL Assays Polylysine (Sigma Chemical, P7890, Average Mol. Wt. 19 kD) was labeled with biotin and TAG1 by the following procedure. Polylysine (11.3 mg) was dissolved in 6.93 mL of PBS-1 and the solution was filtered through a 0.22 um pore size filter. The solution was made basic with triethylamine (38 uL). The polylysine was labeled with TAG1 and biotin by reaction of the lysine amino groups with TAG1-NHS and biotin-LC sulfoNHS (IGEN International), respectively. Aliquots of the polylysine solution (800 uL, 70 nmol of polylysine) was treated with 5 equivalents (per polymer molecule) of biotin-LC sulfoNHS and between 1-100 equivalents (per polymer molecule) of TAG-NHS (by the addition of solutions prepared in DMSO) so as to give polymers comprising a constant small number of biotin moieties and varying numbers of TAG1 groups. After allowing 30 min. for the reactions to proceed to completion, the remaining unreacted amino groups were capped by the addition of an excess of succinic anhydride in DMSO. The polymers were purified by gel filtration chromatography on NAP-5 columns (Pharmacia) using PBS-1 as the eluent. A comparison of the solution fluorescence of polymer-bound TAG1 groups vs. non-polymer bound TAG1 showed similar emission yields indicating that little or no quenching occurs due to the attachment of large numbers of TAG1 moieties on one polymer chain.

Figure 5:
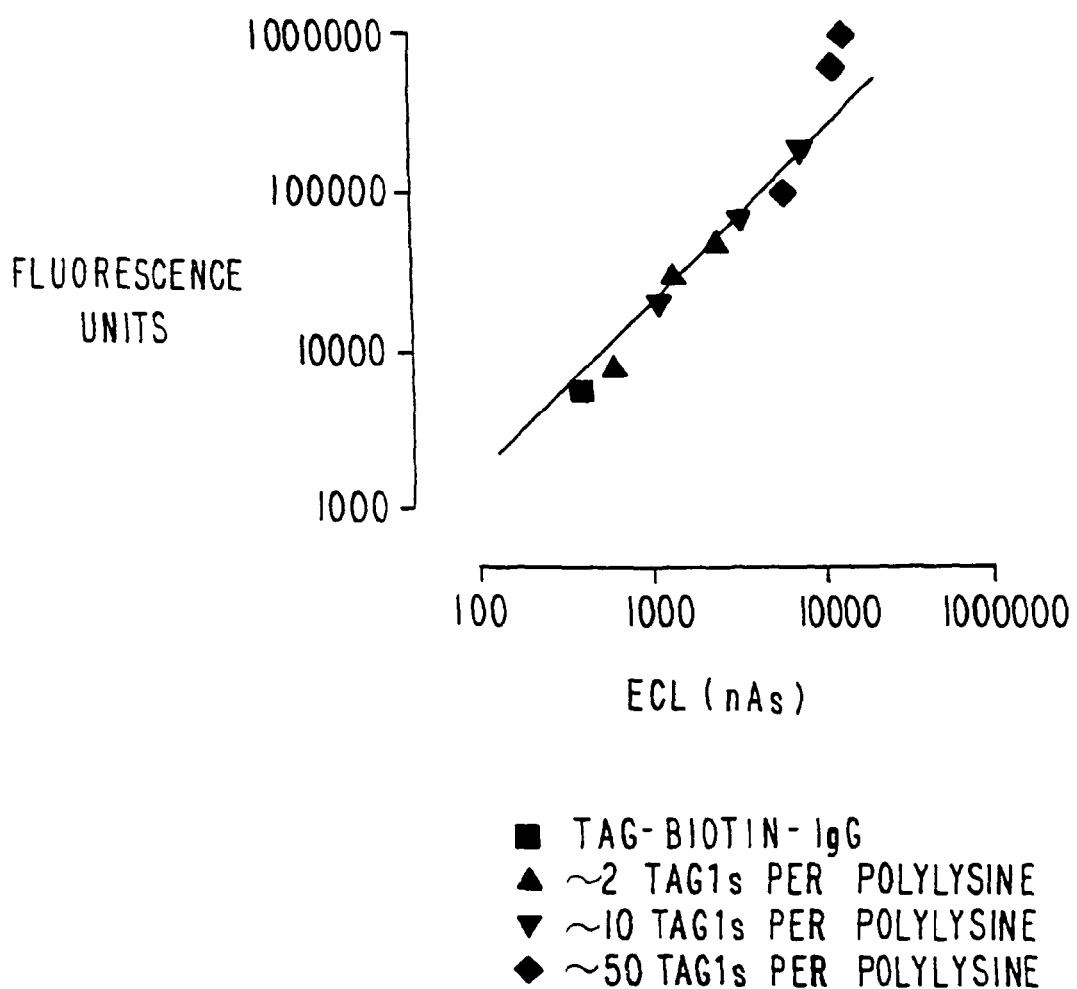
FIG. 5 is a comparison of the ECL signal and surface fluorescence for TAG1 and biotin-labeled polylysines on a streptavidin-coated electrode surface, wherein the data points represent different concentrations of polymer or different ratios of the number of TAG 1 more then per polymer strand.

Several polymers varying in the number of TAG1 moieties per polymer were allowed to bind to streptavidin-coated chromic acid-treated fibril-EVA composite electrodes. The concentrations of the polymers were also varied so that electrodes were produced having varying amounts of each polymer on the surface. After binding, the electrodes were washed with PBS-1 and water to remove excess non-bound polymer. The surface fluorescence due to bound TAG1 moieties was measured at glancing angle using a Photon Technology International Fluorimeter equipped with a solid sample holder (the excitation wavelength was held at 450 nm, the fluorescence signal was determined by integrating the signal obtained by scanning the emission wavelength from 590-620 nm). To measure ECL, the electrodes were placed in an ECL cell and ECL was measured in the presence of ECL Assay Buffer. A log-log plot of fluorescence vs. ECL for the various samples (FIG. 5) shows an approximately linear relationship between fluorescence and ECL (a line with a slope of one is provided for comparison) indicating that ECL can be efficiently induced from polymers linked to multiple ECL labels. The fluorescence and ECL obtained using a biotin- and TAG1-labeled IgG molecule is shown for comparison.

What is claimed is:

1. An apparatus for performing an electrochemiluminescence (ECL) assay for an analyte of interest, comprising: (a) an ECL-inactive electrode having immobilized on its surface a first assay-ligand for said analyte; and (b) an ECL-active microparticle having a second assay-ligand for said analyte immobilized thereon, and an electrochemiluminescent label comprising a ruthenium (Ru) transition metal complex and/or an electrochemiluminescence co-reactant also immobilized on the ECL-active microparticle; wherein said ECL-active microparticle is adapted to (i) carry electrical energy from said electrode surface when said microparticle is bound to said electrode surface through said analyte and (ii) act as an electrode to induce ECL from ruthenium tris(bipyridine) in the presence of tripropylamine, and said ECL-inactive electrode is adapted to induce ECL from ruthenium tris(bipyridine) in the presence of tripropylamine weakly relative to said ECL-active microparticle.

2. The apparatus of claim 1, wherein said electrochemiluminescent label comprises ruthenium tris(bipyridyl) or a derivative thereof.

3. The apparatus of claim 1, wherein said electrochemiluminescence co-reactant is a tertiary amine.

4. The apparatus of claim 1, wherein said ECL-active microparticle comprises a material selected from the group consisting of gold, palladium, platinum, indium and antimony doped tin oxide, polythiophene, and carbon.

5. The apparatus of claim 1, wherein said ECL-inactive electrode comprises a material selected from the group consisting of nickel, stainless steel and chemically oxidized metal.

6. An apparatus for performing an electrochemiluminescence (ECL) assay for an analyte of interest, comprising: (a) an ECL-inactive electrode having immobilized on its surface a first assay-ligand for said analyte; and (b) an ECL-active microparticle having a second assay-ligand for said analyte immobilized thereon, and an electrochemiluminescent label comprising a ruthenium (Ru) transition metal complex and/or an electrochemiluminescence co-reactant also immobilized on the ECL-active microparticle; wherein said ECL-active microparticle is adapted to (i) carry electrical energy from said electrode surface when said microparticle is bound to said electrode surface through said analyte and (ii) act as an electrode to induce ECL from ruthenium tris(bipyridine) in the presence of tripropylamine, and said ECL-inactive electrode is adapted to be incapable of inducing ECL from ruthenium tris(bipyridine) in the presence of tripropylamine relative to said ECL-active microparticle.

7. The apparatus of claim 6, wherein said electrochemiluminescent label comprises ruthenium tris(bipyridyl) or a derivative thereof.

8. The apparatus of claim 6, wherein said electrochemiluminescence co-reactant is a tertiary amine.

9. The apparatus of claim 6, wherein said ECL-active microparticle comprises a material selected from the group consisting of gold, palladium, platinum, indium and antimony doped tin oxide, polythiophene, and carbon.

10. The apparatus of claim 6, wherein said ECL-inactive electrode comprises a material selected from the group consisting of nickel, stainless steel and chemically oxidized metal.

11. The apparatus of claim 1, wherein said assay is a sandwich binding assay, said first assay-ligand and said second assay-ligand are different, and both of said first assay-ligand and said second assay-ligand bind to said analyte.

12. The apparatus of claim 11, wherein said first assay-ligand comprises a first antibody or a first nucleic acid, and said second assay-ligand comprises a second antibody or a second nucleic acid.

13. The apparatus of claim 1, wherein said assay is a competitive binding assay, said first assay-ligand comprises the analyte or an analog thereof, and said second assay-ligand comprises a binding partner of the analyte.

14. The apparatus of claim 1, wherein said assay is a competitive binding assay, said first assay-ligand comprises a binding partner of the analyte, and said second assay-ligand comprises the analyte or an analog thereof.

15. The apparatus of claim 6, wherein said assay is a sandwich binding assay, said first assay-ligand and said second assay-ligand are different, and both of said first assay-ligand and said second assay-ligand bind to said analyte.

16. The apparatus of claim 15, wherein said first assay-ligand comprises a first antibody or a first nucleic acid, and said second assay-ligand comprises a second antibody or a second nucleic acid.

17. The apparatus of claim 6, wherein said assay is a competitive binding assay, said first assay-ligand comprises the analyte or an analog thereof, and said second assay-ligand comprises a binding partner of the analyte.

18. The apparatus of claim 6, wherein said assay is a competitive binding assay, said first assay-ligand comprises a binding partner of the analyte, and said second assay-ligand comprises the analyte or an analog thereof.

* * * * *